United States Patent [19]
Hackett

[11] Patent Number: 5,448,923
[45] Date of Patent: Sep. 12, 1995

[54] SCORED METAL SLAG COVERS FOR MOLTEN SAMPLER INTAKE PORTALS

[75] Inventor: Robert J. Hackett, Brookfield, Conn.

[73] Assignee: Haly Inc., Brookfield, Conn.

[21] Appl. No.: 313,443

[22] Filed: Sep. 27, 1994

[51] Int. Cl.$^6$ .............................................. G01N 1/12
[52] U.S. Cl. ................................ 73/864.58; 73/864.59
[58] Field of Search ............ 73/864.58, 864.53, 864.59

[56] References Cited

U.S. PATENT DOCUMENTS

| | | | |
|---|---|---|---|
| 3,452,602 | 7/1969 | Hackett | 73/864.58 X |
| 3,457,790 | 7/1969 | Hackett | 73/864.58 X |
| 3,561,494 | 2/1971 | Hackett | 138/177 |
| 3,577,886 | 5/1971 | Wiese | 73/864.58 X |
| 3,686,949 | 8/1972 | Hackett | 73/864.58 X |
| 3,791,219 | 2/1974 | Falk | 73/864.58 X |
| 3,905,238 | 9/1975 | Falk | 73/864.58 X |
| 4,046,016 | 9/1977 | Hackett | 73/864.58 X |
| 4,116,070 | 9/1978 | Falk | 73/864.58 X |
| 4,453,424 | 6/1984 | Hackett | 73/864.58 |
| 4,499,777 | 2/1985 | Hackett | 73/804.56 |
| 4,875,380 | 10/1989 | Boron | 73/864.58 |
| 5,014,561 | 5/1991 | Falk et al. | 73/864.58 X |

Primary Examiner—Thomas P. Noland
Attorney, Agent, or Firm—Ware, Fressola, Van Der Sluys & Adolphson

[57] ABSTRACT

A chill mold sampler for molten metal, capable of taking pin samples or flat disc samples or both, has one or more high melting point quartz glass intake tubes, each with a portal end closed by a thin metal slag cover cemented in place, blocking the entry portal during the plunging sampling immersion of the sampler into the melt. Two or more paper covers cemented over the outside of the metal slag cover provide explosive deflection of slag during the plunging entry of the sampler into the molten metal. A narrow scored groove or slit formed at least partway across the face of the metal slag cover permits rapid melting of the metal cover at low temperatures, just at or above the "liquidus" or freezing temperature of the melt, immediately after passage of the sampler through the hot slag layer, achieving successful sampling of fully deoxidized or "dead" killed steels. For very low carbon steel melts, thin metal slag covers of comparable very low carbon steel produce accurate samples, and avoid introducing undesired carbon to the samples. For unkilled steel, low temperature melt sampling can be achieved by enclosing a few helical turns of a coil of de-oxidant wire between the intake portal and its thin grooved or slit metal slag cover.

9 Claims, 2 Drawing Sheets

SCORED METAL SLAG COVERS FOR MOLTEN SAMPLER INTAKE PORTALS

TECHNICAL FIELD

This invention relates to molten metal sampling devices, and particularly to samplers incorporating insulated metal chill molds mounted at the extreme end of an insulated metal lance tube for plunging immersion through the slag layer into a body of molten metal, a portion of which rushes into the sampler chill-mold cavity which is then quickly withdrawn from the melt and quenched if necessary, producing a solidified sample of the molten metal.

BACKGROUND ART

Many different types, shapes and components of samplers for molten metal have been developed or proposed in recent years. These include the samplers disclosed in my previous U.S. Pat. Nos. 3,457,790; 3,452,602; 3,686,949; 4,046,016; 4,499,777 and 4,453,424. The foamed ceramic or castable silicate compositions described in my U.S. Pat. No. 3,561,494 provide excellent heat insulating coatings protecting samplers and lance tubes from the high temperature molten metal during the sampling operation, and assuring proper chilling of the melt samples.

A sampler for molten metal must provide a sampling chamber or cavity enclosed inside a hollow chill mold, which is provided with slots or vents capable of venting the air displaced by the inrushing molten metal. Surrounding insulating material, such as a foamed ceramic chamber or coating, preserves the chill mold at a temperature far below that of the molten metal for a period long enough to chill the inrushing molten sample to the consistency of slush. The sampler is then removed from the melt, and cooling is continued by exposure to the atmosphere at room temperature, or to a quenching bath of water or liquid nitrogen, for example.

The solidified samples are then readily removed from the chill mold for prompt metallurgical analysis, facilitating immediate adjustment of the melt composition as often as required while still in its molten state.

The samplers of these previous patents produce reliable and homogeneous samples whether they are used in deep immersion sampling operations, killed steel sampling operations requiring no deoxidizing treatment, or sampling of unkilled steel with deoxidants carried inside the sampler being dispersed and dissolved in the inrushing molten metal as the sampling operation is performed. Metallic deoxidants such as aluminum, zirconium, magnesium, or titanium are preferably formed in the shape of a helical coil of wire, positioned just inside a slag cover at the intake portal of the sampler, as illustrated in FIG. 11 of my U.S. Pat. No. 4,499,777.

Sampling of low temperature melts, such as those just at or above the "liquidus" or "freezing" temperature at which the molten metal begins to solidify, imposes unique problems. The sampler must be protected from the effects of floating slag which must not be allowed to freeze on the cold sampler and block the sampling operation. At the same time, the metal slag cover protecting the intake portal of the sampler must not be so thick as to retard the melting of the slag cover and thus unnecessarily delaying the entrance of the molten metal to be sampled to the interior of the sampling chill mold.

Accordingly, a principal object of the present invention is to provide highly effective molten metal sampling for use in relatively low temperature molten metal.

Another object of the invention is to provide sampler devices capable of such sampling with metal slag covers over their intake portals which are readily melted away, even by the low temperature molten metal.

A further object of the invention is to provide such samplers in which the metal slag covers are enclosed in protective jackets capable of explosive slag deflection during the immersion of the sampler in the melt.

A still further object of the invention is to provide such samplers incorporating a predetermined volume of deoxidant material encircling the intake portal inside the metal slag cover.

Other objects of the invention will in part be obvious and will in part appear hereinafter.

The invention accordingly comprises the features of construction, combinations of elements, and arrangements of parts which will be exemplified in the constructions hereinafter set forth, and the scope of the invention will be indicated in the claims.

BRIEF SUMMARY OF THE INVENTION

The improved intake portal assemblies of the present invention are characterized by a high temperature quartz glass portal tube extending from the interior of a protective chill mold sampler casing or enclosure, preferably formed of two mating halves of foamed ceramic heat insulating material. The interior end of each quartz glass tube forms a chill mold, or is connected inside the enclosure to a chill mold formed of metal with numerous gas escape vent slots formed therein. The external end of the quartz glass tube is exposed to the space outside the enclosure and forms an intake portal for the sampler. This exposed intake portal end of each of these quartz glass portal tubes is protected by a cup-shaped thin metal cap cemented in place surrounding and blocking the open quartz glass intake portal. The cup-shaped metal slag cover is formed with a deep-drawn cylindrical skirt portion extending along and telescopingly enclosing the outer periphery of the quartz glass tube adjacent to its open portal end, and is cemented in place thereon by a thin bead ring of "Duco" cement, sturdily anchoring the metal slag cover on the portal end of the quartz glass tube.

The metal slag cover is preferably formed of thin sheet metal, and the central portion of this sheet metal directly spanning the intake portal entrance of the quartz glass tube is preferably provided with a diametric groove over at least the central portion of a diameter, significantly reducing the actual thickness of the metal slag cover in this region. This groove may be stamped or formed across the interior face of the metal slag cover, and in some cases, may actually penetrate the thickness of the sheet metal slag cover, forming a slit thereof.

In all cases, however, the exterior of the metal slag cover is enclosed in a protective slag deflector jacket preferably formed of paper or a similar cellulose composition in two or more layers, which are themselves cemented over the outside of the metal slag cover.

The outer surfaces of the quartz glass tubes are preferably covered by a coating of refractory silicate grout extending from the slag deflector to the sampler casing enclosure, protecting the tubes and the mating butt seams of the mating sampler casing enclosure halves from the high temperature slag and the even higher temperature molten metal.

Upon immersion of the sampler into the molten metal, the protective paper layers enclosing the metal slag cover are heated to their combustion temperature so quickly that they essentially "explode", driving away floating slag which might otherwise tend to freeze on the cold sampler, and to coat its external surface. This explosive deflection of the floating slag allows the sampler to be immersed quickly through the slag layer into the molten metal without any slag coating adhering thereon, exposing the thin sheet metal cover on the intake portal of the sampler directly to the molten metal.

Even at relatively low melt temperatures, close to the freezing temperature of the melt, the thin scored portion of the metal cover exhibits negligible resistance to the transmission of heat from the melt. This scored metal slag cover portion rapidly melts, admitting the molten metal to the interior of the intake portal tube and the chill mold of the sampler, driving ahead of it the air contained in the chill mold through the various slots communicating with the interior of the supporting lance tube held by the operator.

If deoxidant is enclosed between the metal cover and the intake portal, the inrushing melt quickly dissolves it and distributes it uniformly throughout the portion of the molten metal forming the sample in the chill mold, thus equating the composition of the deoxidized sample with the predicted final deoxidized composition of the molten metal just before it is poured or cast.

THE DRAWINGS

For a fuller understanding of the nature and objects of the invention, reference should be made to the following detailed description taken in connection with the accompanying drawings, in which.

BEST MODE FOR CARRYING OUT THE INVENTION

Figure 1:
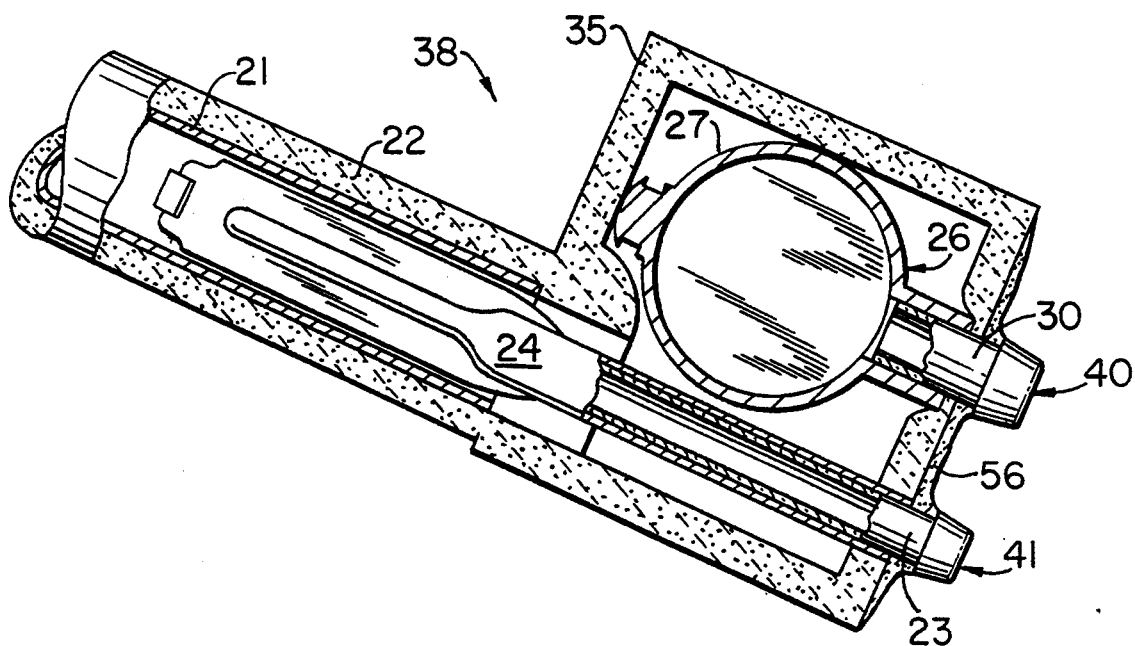
FIG. 1 is a fragmentary sectional side elevation view partially broken away showing a disc sample chill mold and a pin sample chill mold both enclosed in a heat resistant sampler chamber enclosure mounted at the end of a lance tube, with each chill mold being provided with an intake portal tube protruding forwardly for exposure to the molten metal as the sampler is immersed in the melt.

The double chill mold sampler illustrated in FIG. 1 corresponds to the device shown in FIG. 10 of my U.S. Pat. No. 4,499,777. The sampler assembly 38 is installed in a protective refractory sampler chamber enclosure 35 at the end of a hollow cylindrical steel lance tube 21 having a layer 22 of laminated paper or foamed ceramic insulation surrounding its entire periphery and serving to protect the lance tube 21 from the heat of the molten metal in which it is immersed. The lower sampling chill mold shown in FIG. 1 is a long hollow ceramic pin sample mold, preferably formed as a tube 23 of quartz glass capped by a slag deflector 41 and closely embraced inside a slotted riser vent assembly 24 supporting the chill mold tube and venting from it into the interior of lance tube 21 the air displaced by the inflowing molten metal filling the sampler.

Figure 5:
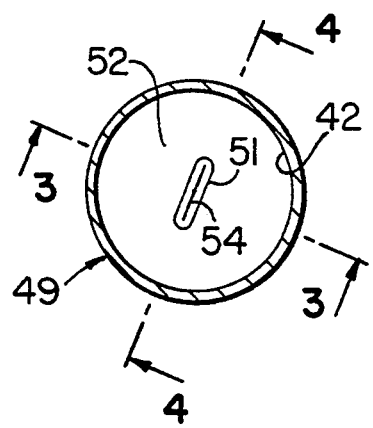
FIG. 5 is a rear elevation view on a reduced scale of the metal slag cover of FIG. 4, showing planes 3—3 and 4—4 on which the previous views are taken.
Figure 6:
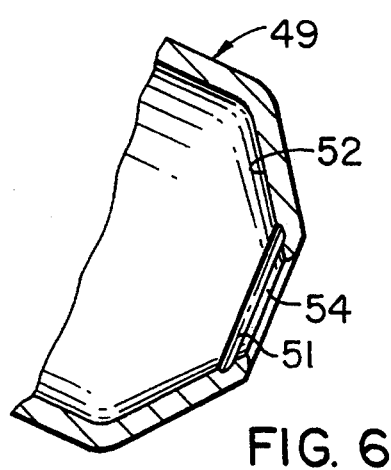
FIG. 6 is a cross-sectional elevation view similar to FIG. 4, showing a modified embodiment of the metal slag cover.

Suitable slotted riser vents are shown in my U.S. Pat. No. 4,046,016, and as riser vents 20 illustrated in FIGS. 5 and 6 of my U.S. Pat. No. 4,453,424. The riser vent 24 is preferably made in two semi-cylindrical halves having their distal ends pivotally connected for engagement, as illustrated in FIGS. 5 and 7 of that U.S. Pat. No. 4,453,424, leaving significant slots between their mating edges through which air is vented, as it is displaced by the molten metal, into the interior of lance tube 21, through which it passes to the atmosphere.

Shown in FIG. 1 above the pin sampler mold tube 23 is a disc sampler chill mold 26 with a quartz glass intake portal tube 30, capped by a slag deflector 40. Chill mold 26 is formed by two ring-shaped mold halves 27 each having an internal outward facing shelf 28 on which a disc cover plate 29 is superimposed in peripherally spaced relationship. A long vent slot around the entire periphery of the disc sampler mold halves 27 is provided by their central rims facing each other and spaced apart by raised lands formed directly on the facing rims of the two disc sampler mold halves 27, thereby forming between these lands a peripheral vent slot between these two halves in their assembled position, all as shown and described in my U.S. Pat. No. 4,499,777 with particular reference to FIGS. 4 through 10.

Double chill mold samplers of the kind illustrated in FIG. 1 have proved to be highly successful samplers in the steel industry, particularly useful for sampling expensive high quality alloy steels whose compositions must be sampled at different times during its manufacture in order to assure the desired composition for the final alloy. The time and sampler materials expended in these repeated sampling operations are well justified by the quality control achieved thereby.

Figure 2:
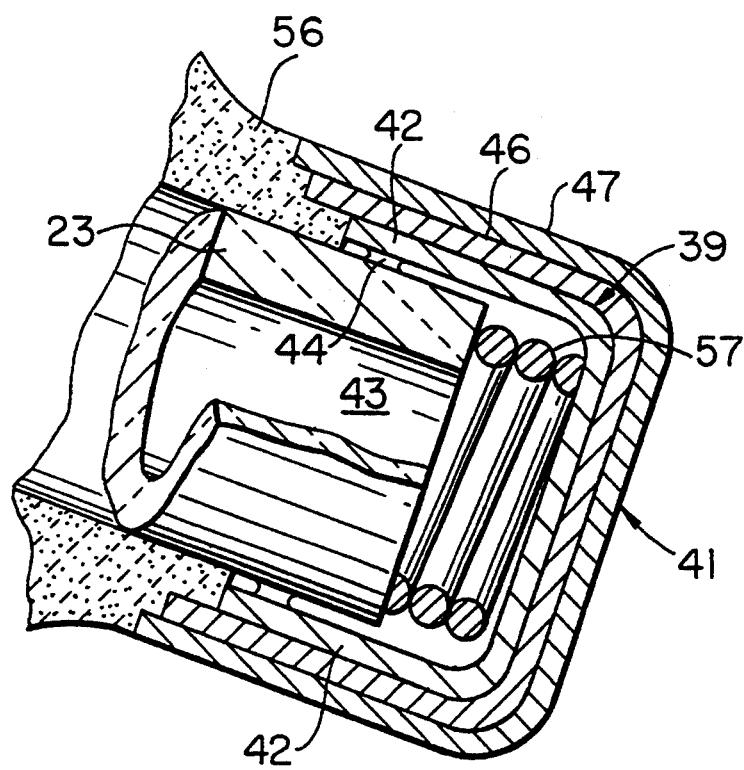
FIG. 2 is a greatly enlarged fragmentary cross-sectional elevation view of one of the intake portals shown in FIG. 1, illustrating one embodiment of the present invention.

The slag cover and deflector assembly 41 shown in FIG. 2 incorporates a deep-drawn thin sheet steel portal cover 39 having a cylindrical skirt portion extending longitudinally in the axial direction to overlap by a significant distance the proximal portal end 43 of the quartz intake tube 23. A ring-shaped bead 44 of refractory cement encircles the quartz glass intake tube 23 inside the overlapping portion of the cover's side skirt 42, anchoring the metal portal cover 39 firmly on the intake portal end 43 of the tube 23.

Cemented to the exterior of the sheet metal cover 39 is a first paper slag-deflecting cover 46 formed in a cup shape and dimensioned for close interfitting engagement overlapping the exterior of the metal cover 39, for adhesive mounting thereon. A second paper slag-deflecting cover 47 is correspondingly mounted in close interfitting telescoping engagement for adhesive bonding to the outer surface of the first slag cover 46. Ceramic refractory grout 56 coating quartz glass tubes 23 and 30 behind paper slag covers 46 and 47 protects the exterior of tube 23 and the exterior surface of enclosure 35 from hot slag and molten metal during immersion. These double paper slag-deflecting covers have been found to provide the kind of explosive deflection of the floating slag during immersion of the cold sampler in the melt which is most effective to avoid any accumulation or "freezing" of slag on the metal portal cover 39.

Figure 3:
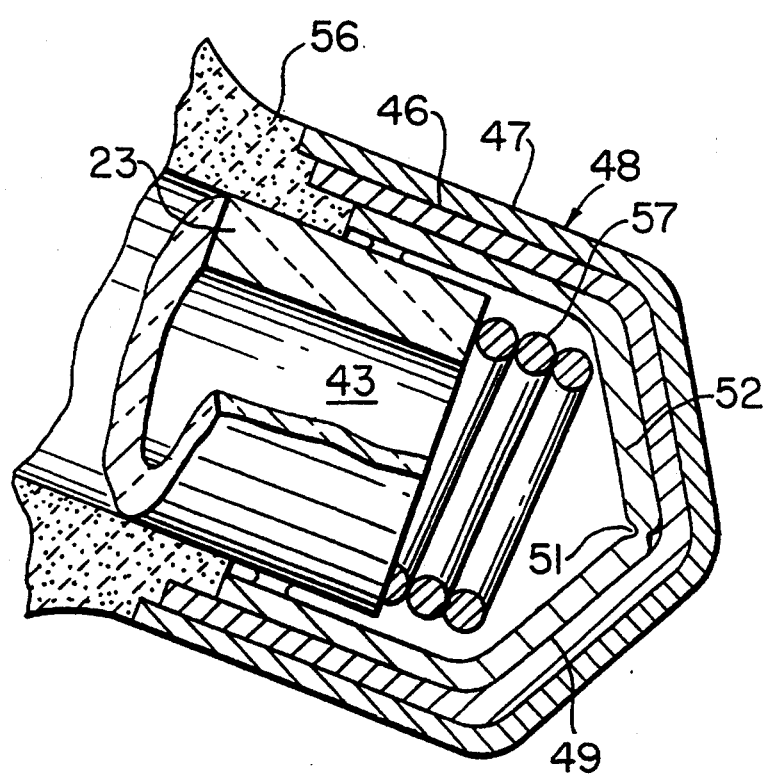
FIG. 3 is a corresponding greatly enlarged fragmentary cross-sectional side elevation view of a similar intake portal tube incorporating a second embodiment of the invention.

In the second embodiment of the present invention shown in FIG. 3, a slightly different shape of slag cover assembly 48 is illustrated, with the sheet metal portal cover 49 having a deep drawn skirt portion 42 like that shown in FIG. 2, and a generally convexly domed conical or peaked proximal end portion covering the portal end 43 of the quartz glass sampler tube 23, with a central scored groove 51 extending at least partway across a diameter of the peaked portion 52.

Figure 4:
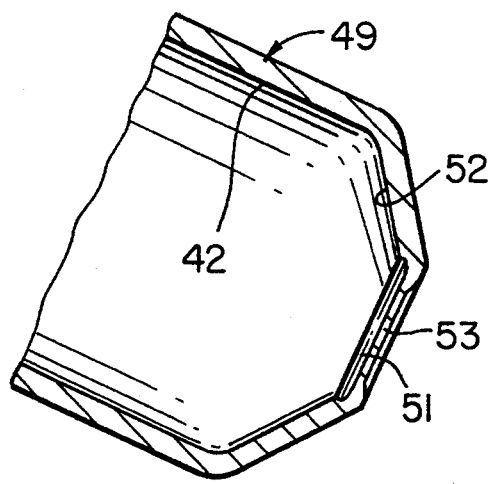
FIG. 4 is a greatly enlarged cross sectional side elevation view of the metal slag covers incorporated in the assembly of FIG. 3.

As illustrated in FIGS. 3, 4 and 5, the groove 51 leaves a thin wall portion 53 in the central conical part 52 of the cover 49. Thin cover portion 53 offers little resistance to the temperature or pressure of the molten metal to which it is exposed immediately after the paper covers 46 and 47 are explosively evaporated by the high temperature of the slag through which the sampler is immersed. As a result, the molten metal, even at temperatures close to the liquidus or freezing temperature, immediately forces its way through the cover 49 and rapidly flows into the portal 43 and up the quartz glass sampler tube 23. In the same manner, the quartz glass sampler tube 30 serving as the portal for the disc sampler 26 shown in the upper portion of FIG. 1 may be provided with either of the cap assemblies shown in FIGS. 2 or FIG. 3 to provide highly effective sampling, forming a disc sample for spectrophotometry or X-ray laboratory testing.

If groove 51 is so deep that it leaves negligible thickness in the thin portion 53 of the deep drawn cover 49, portion 53 may actually be formed as a slit 54 (FIG. 6) communicating between the interior and exterior of the cover 49 and offering even less resistance than a thin-walled portion 53 would offer to the advance of the inrushing molten metal. In this instance the slit metal portal cover 49 serves primarily as a support for the two paper slag-deflecting covers 46 and 47 during the rapid immersion of the sampler through the floating slag.

A very low carbon steel may be used for forming the deep-drawn sheet metal portal covers 39 or 49, thus having a negligible effect upon the carbon content of the resulting sample formed in the chill mold. When "killed" steel having a very low oxygen content is being sampled, deoxidant materials may not be needed in the samplers of the present invention. However, as shown in FIGS. 2 and 3, a helical coil of wire deoxidant material 57 dimensioned to encircle the intake portal 43 of the quartz glass sample tube 23 between the portal end of the tube and the metal cap overlapped and telescopingly mounted thereon may be incorporated in the assemblies of this invention whenever desired, to permit the sampling of unkilled steel with the required amount of deoxidant material.

It will thus be seen that the objects set forth above, and those made apparent from the preceding description, are efficiently attained and, since certain changes may be made in the above construction without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A chill mold assembly for collecting, chilling and withdrawing a sample from a body of molten metal having an overlying slag layer, comprising
   A. an elongated, hollow, heat-insulated lance tube having a sampling end and an open handle end exposed to the atmosphere,
   B. a slot-vented chill mold secured to the sampling end of the lance and having an open protruding portal end protected by a thin metal cap and a vented end exposed to the hollow interior of the lance's sampling end,
   C. a heat-insulating enclosure isolating the slot-vented chill mold from the surround, and
   D. a plurality of paper layers forming a protective jacket secured to the external surface of said thin metal cap, whereby immersion of the chill mold enclosure on the sampling end of the lance tube into the overlying slag layer produces explosive evaporation of the paper layers, deflecting the hot slag and exposing the external surface of the thin metal cap directly to the molten metal under the slag layer with no slag coating fused thereon.

2. The chill mold assembly defined in claim 1, further including a coil of deoxidant metal wire, formed of material selected from the group consisting of aluminum, magnesium, titanium and zirconium, enclosed between the open portal end of the chill mold and the thin metal cap.

3. The chill mold assembly defined in claim 1, wherein the thin metal cap is formed with a scored groove extending at least partway across it, whereby the thickness of the cap is reduced, in the region of said groove, relative to the thickness of the balance of said metal cap.

4. The chill mold assembly defined in claim 3, wherein said scored groove over a substantial portion of its length penetrates through the thin metal cap, thereby forming a slit.

5. The chill mold assembly defined in claim 3 wherein the thin metal cap is formed with a deep drawn skirt portion telescopingly embracing said protruding portal end of said chill mold and adhesively bonded thereto.

6. The chill mold assembly defined in claim 5 wherein the thin metal cap is formed with a substantially flat central portion spanning the open portal end of said chill mold.

7. The chill mold assembly defined in claim 5 wherein the thin metal cap is formed with a convex domed central portion extending beyond said open portal end of said chill mold.

8. The chill mold assembly defined in claim 1, further including a ceramic refractory grout coating surrounding the peripheral surface of the protruding portal end from the protective jacket to the heat-insulating enclosure.

9. The chill mold assembly defined in claim 8, wherein the grout coating extends over a substantial part of the external surface of the heat-insulating enclosure.

* * * * *